United States Patent [19]

Zand et al.

[11] Patent Number: 5,142,045
[45] Date of Patent: Aug. 25, 1992

[54] ELECTROACTIVE MATERIALS

[75] Inventors: Robert Zand, Ann Arbor, Mich.; Shinji Nezu, Bay Village, Ohio; Selim Kusefoglu, Istanbul, Turkey

[73] Assignees: Aisin Seiki Kabushiki Kaisha, Kariya City, Japan; The Regents of the University of Michigan, Ann Arbor, Mich.

[21] Appl. No.: 199,764

[22] Filed: May 27, 1988

[51] Int. Cl.⁵ .................... C07D 279/18; H01B 1/06
[52] U.S. Cl. .................................. 544/40; 252/500; 252/518
[58] Field of Search .................. 252/500, 518; 544/35, 544/37, 38, 39, 40; 528/422, 423, 183, 210, 342

[56] References Cited

U.S. PATENT DOCUMENTS

| | | | |
|---|---|---|---|
| 4,505,841 | 3/1985 | Denisevich | 252/500 |
| 4,505,843 | 3/1985 | Suzuki et al. | 252/500 |

OTHER PUBLICATIONS

Lambrou et al., "Nouveaux Derives de la Phenothiazine", *Eur. J. Med. Chem.*, Sep.-Oct. 1977, vol. 12, No. 5, p. 488.

*Primary Examiner*—Josephine Barr
*Attorney, Agent, or Firm*—Burns, Doane, Swecker & Mathis

[57] ABSTRACT

Novel polymers containing 6,6,6-tricyclic moieties pendant from the polymer backbone, their novel monomers, and novel conductive polymers formed by doping the novel polymers with an electron acceptor compound. The novel polymers are easily synthesized, are soluble in various solvents, and are more stable than conductive polymers having the tricyclics as repeating units in the polymer backbone. A preferred tricyclic is phenothiazine.

4 Claims, 1 Drawing Sheet

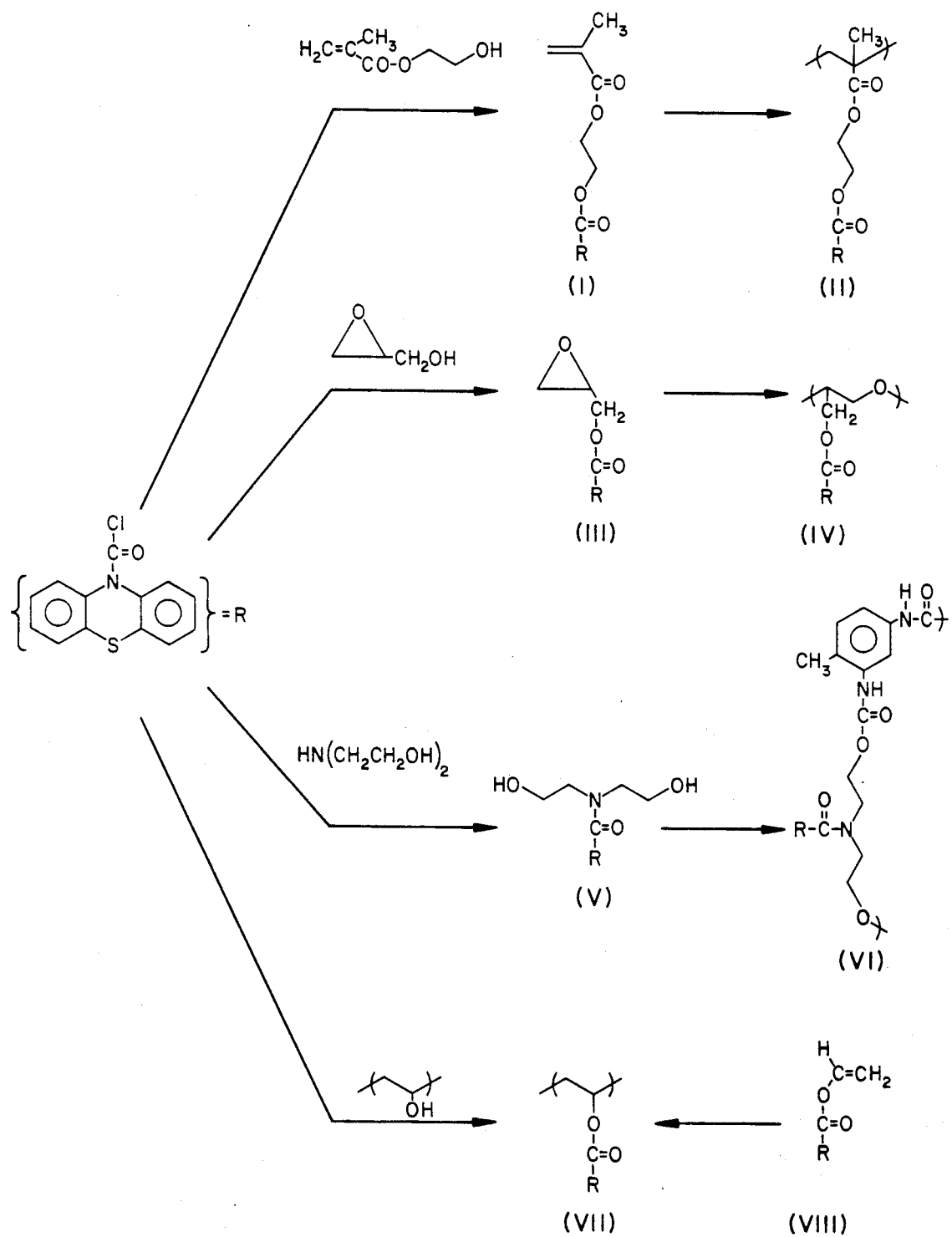

ELECTROACTIVE MATERIALS

BACKGROUND OF THE INVENTION

The invention relates to electroactive organic materials and more particularly to novel electroactive polymers and their synthesis. In particular, the invention is directed to polymers having 6,6,6-membered tricyclic moieties as pendant groups. The groups act as electron donors which, in the presence of an electron acceptor dopant, render the polymer conductive.

Electronic properties of a polymer containing an electroactive pendant group depend on electron transfer between adjacent or nearby pendant groups. Therefore the orientation, stacking and proximity of the pendant groups is a major determining factor in the success of a given polymer as an electroactive polymer. These properties, in turn, depend on the repeating unit length, spacer group length and the conformational requirements of the polymer backbone.

Polymers that contain electroactive groups as pendant groups or as a part of the polymer backbone are of considerable interest as electrode modifiers, in polymeric redox systems and in photo- and semiconductors. A number of aromatic heteropolycyclic compounds, among them phenothiazine and its derivatives, have been shown to have semiconduction, electron donation and photoconduction properties. Polymers containing phenothiazine can be used as redox polymers and semiconducting and charge transfer polymers. The benzene ring-substituted derivatives of phenothiazine are known to be effective free radical scavengers, which prevents their use as vinyl monomers. However, the N-substituted phenothiazine derivatives, such as N-vinyl and N-acrylyl phenothiazine, undergo free-radical addition polymerization with ease.

U.S. Pat. No. 4,505,841 discloses electroactive polymeric materials which are said to be soluble in various solvents. The polymers are comprised of recurring units of fused unsaturated 6,6,6-membered heterocyclic rings wherein the central ring contains the heteroatoms. Charge compensating ionic dopants are associated with the polymers. Phenothiazine polymers, in which the heteroatoms are nitrogen and sulfur, are disclosed, whereby phenothiazine repeating units are incorporated into the backbone of the polymer.

One of the problems associated with prior art conductive polymers in general is their insolubility in organic or aqueous solvents. Because of this, the polymers are very difficult to process into usable forms, such as films, etc.

Another problem of some prior art conductive polymers is that the electrical conductivity decreases over time, possibly due to oxidative effects.

DISCLOSURE OF THE INVENTION

It is accordingly an object of the invention to provide a polymer containing conductive 6,6,6-tricyclic pendant groups, such as phenothiazine, and which is soluble in a solvent and therefore capable of being easily processed.

It is another object of the invention to provide a polymer, as above, which is easily synthesized.

It is yet another object of the invention to provide a polymer, as above, having conductive properties which are stable over time.

These objects are achieved by a compound of the formula:

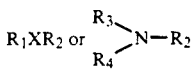

wherein $R_1$ is a group with monomer functionality capable of homo- or copolymerization, X is a divalent moiety pendant from $R_1$ and comprising -COOR$_5$O-, -R$_6$O- or -O-, $R_2$ is

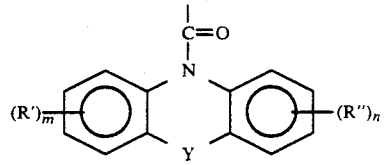

$R_3$ and $R_4$ are separately hydroxyalkyl having from 1 to 5 carbon atoms, $R_5$ and $R_6$ are alkylene having from 1 to 5 carbon atoms, m and n are separately integers from 0 to 4, R' and R'' are alkyl from 1 to 5 carbon atoms, oxyalkyl from 1 to 5 carbon atoms or halogen, and Y is carbon or a heteroatom selected from N, O and S.

The objects of the invention are also achieved by novel homopolymers and copolymers formed from the above compounds, both alone and in combination with a dopant which acts as an electron acceptor. Suitable dopants include halogens ($I_2$, $Br_2$, etc.), $AsF_5$, tetracyanoethylene, 7,7,8,8 tetracyanoquinodimethane and similar electron acceptors known to participate in charge transfer complex formation.

BRIEF DESCRIPTION OF THE DRAWING

For a full understanding of the invention, reference should be made to the following detailed description and the drawing, which outlines the synthesis of some of the various monomers and polymers that are described hereinafter.

DETAILED DESCRIPTION OF THE PREFERRED EMBODIMENTS

The polymers disclosed hereinafter have different repeating group and spacer group lengths as well as different backbone flexibilities and are designed to serve as semiconductors, redox polymers, photoconductors and electrode modifiers.

The monomers are produced by the Schotten Bauman reaction of the corresponding 6,6,6-tricyclic N-carbonyl chloride with a suitable nucleophilic agent. A preferred tricyclic is phenothiazine in which "Y" of the above formula for $R_2$ is sulfur. While the discussion hereinafter refers to phenothiazine alone, it is to be understood that tricyclics other than phenothiazine which are encompassed by the above formula, are contemplated.

The synthesis and electrical properties of the following new compounds are outlined in the Figure: ethylene glycol-methacrylate phenothiazine N-carboxylate bisester (I) and its homopolymer (II); glycidyl phenothiazine N-carboxylate (III) and its homopolymer (IV); phenothiazine N-carboxylate diethanolamide (V) and its polyurethane formed with toluene diisocyanate (VI); and phenothiazine N-carboxylate-polyvinyl alcohol polyester (VII).

The Schotten Bauman reaction between phenothiazine N-carbonyl chloride and hydroxyethyl methacrylate (HEMA) to produce compounds I and II involves side reactions. Examination of the liquid phase reveals the presence of pyridine, unreacted HEMA, phenothiazine and ethylene glycol, indicating that both starting materials undergo hydrolysis reactions to some extent. It is further noted that the bulk polymerization of monomer (I) is accompanied by some pressure build-up. When the gas evolved from the reacting mixture is bubbled through a barium hydroxide solution, a white precipitate is observed, indicating the presence of carbon dioxide. The thermal decarboxylation of phenothiazine N-carboxylate esters to yield phenothiazine, carbon dioxide and the corresponding alcohol has been known.

Solution polymerization at a lower temperature and with more homogeneous heat transfer dominates the problem of thermal decarboxylation and gives better yields of polymer that are wholly soluble in a number of organic solvents and that are film castable. Solutions of polymer (II) turns green and solid polymer (II) turns red upon exposure to light, indicating photosensitivity. However, there are no observable NMR spectral differences between the colorless and colored samples. These polymers could thus be used in electrochromographic applications. Dilute solution viscosity (DSV) measurement of polymer (II) indicates a limiting viscosity of 0.49 dl/g (chloroform, 25° C.). Polymer (II) has a repeating unit length of 2 atoms and a spacer group length of 6 atoms.

Synthesis of monomer (III) cannot be facilitated by the use of common Schotten Bauman reaction catalysts. Potassium hydroxide, pyridine and dimethylaminopyridine all result in the polymerization of glycidol itself. The uncatalyzed reaction is also temperamental, sometimes leading to uncontrollable exothermic glycidol polymerization. A large excess of glycidol is necessary to obtain reasonable yields and no HCl gas evolution could be observed due to considerable solubility of this gas in glycidol. Attempts to remove excess glycidol by titration with water, in which it is soluble, leads to the hydrolysis of the product, presumably to give phenothiazine N-carboxylic acid (a carbamic acid), which decomposes readily. Polymerization of the glycidyl ester is straightforward and the resulting polymer had a dilute solution viscosity of 0.29 dl/g (in chloroform, 25° C.). The polymer (IV) has a repeating unit length of 3 atoms and a spacer group length of 3 atoms and also has a highly polarizable oxygen atom in its backbone.

Phenothiazine N-carboxylate diethanolamide (V) has utility as a pharmaceutical but no synthetic or spectral information is available. Reasonable yields of the product can be obtained by using two equivalents of the amino alcohol where half of the material is protonated by the HCl evolved and is subsequently removed by washing with water. The polymer (VI) made by the polycondensation of the diol with toluene diisocyanate does not seem to be linear since only a portion of any given sample truly dissolves while the rest merely swells. No reliable solution viscosity can be obtained. The polymer is air unstable and cannot be dried to constant weight under vacuum. Some aliphatic polyurethanes are known to behave in a similar manner. This polymer has a 14 atom repeating unit and a 1 atom spacer group as well as a stiff paraphenylene group in the backbone.

Attempted synthesis of phenothiazine N-carboxylate vinyl (VIII) using acetaldehyde, ethyl vinyl ether and vinyl acetate was unsuccessful. To obtain the polymer (VII) by grafting the carbonyl chloride onto an already existing backbone, namely polyvinylalcohol, was attempted. This would give the same polymer as the one theoretically obtainable by polymerization of the vinyl ester. Only 85% of the hydroxyl groups could be substituted and increasing reagent concentration or reaction time does not improve the yield. IR spectroscopy clearly shows the presence of unreacted hydroxyl groups.

Electrical resistance of iodine doped polymers is shown in Table 1. Vapor phase doping and solution doping of iodine give essentially the same iodine uptake and the same resistivity values. The reproducibility of the resistivity values is not very high and it is believed that only the order of magnitude of the specific resistance values are reliable. The redox behavior of the polymers disclosed herein was characterized by cyclic voltammetry. All the polymers showed reversible, one-electron oxidation waves in the triangular-wave voltammograms. The anodic peak potentials and the corresponding cathodic peak potentials are summarized in Table 2.

TABLE 1

Specific Resistance of Iodine Doped Polymers

| Polymer | % Wt. Iodine | Phenothiazine:$I_3$ Molar Ratio | Specific Resistance $\Omega$-cm |
|---|---|---|---|
| II | 21.9 | 3.8:1 | $1.7 \times 10^2$ |
| IV | 33.0 | 3.7:1 | $1.3 \times 10^2$ |
| VI | 28.0 | 1.8:1 | $2.9 \times 10^3$ |
| VII | 10.0 | 1.1:1 | $8.9 \times 10^2$ |

TABLE 2

| | Anodic Peak Potential | | |
|---|---|---|---|
| Polymer | $E_{p,a}$ mV | $E_{p,c}$ mV | $E_{p,a} - E_{p,c}$ |
| II | 548 | 489 | 59 |
| IV | 589 | 528 | 61 |
| VI | 575 | 513 | 62 |
| VII | 675 | 618 | 58 |

Anodic Peak Potential ($E_{p,a}$), Cathodic Peak Potential ($E_{p,c}$), and Peak Potential Separation ($E_{p,a} - E_{p,c}$) in 0.1M LiClO$_4$/CH$_3$CN at Pt electrode: scan rate 40 mV/s: versus Ag/AgCl reference electrode.

The polymers of the invention are soluble in a number of commonly used organic solvents such as dimethylsulfoxide (DMS), dimethylformamide (DMF) and acetonitrile. One skilled in the art could readily ascertain the solubility characteristics of the polymers in other solvents as well. With respect to stability of the polymers of the invention, since the phenothiazine groups are not in the polymer backbone, conjugation in the backbone is not the mechanism by which the polymer is rendered conductive, and hence oxidation of the polymer, which can break conjugated double bonds, has little if any effect on conductivity. By contrast, conductive polymers such as polyacetylene, which rely on backbone conjugation for their conductive properties, are less stable.

The following examples illustrate the synthesis of some of the compounds of the invention.

EXAMPLE 1

Ethylene glycol-methacrylate phenothiazine
N-carboxylatebis-ester (I)

Phenothiazine N-carbonyl chloride, 3.0 g (12 mmol), 12.0 ml of hydroxyethylmethacrylate (HEMA) and 4 ml of pyridine were mixed. An exothermic reaction started immediately. The mixture was kept at 60° C. for 1 hour and overnight at room temperature. Then 20 ml of water was added dropwise with cooling till a dark gummy solid precipitated. The liquid was decanted and the solid was dissolved in chloroform, washed with 5% aq. HCl and water, treated with charcoal, dried and evaporated to dryness. The resulting tan solid was recrystallized from a minimum amount of ethanol to give the product: 2.2 g (52%), white fluffy crystals, m.p. 64°–65.5° C.

NMR: (Solvent) (Chemical Shift, integration, multiplicity, assignment) ($CDCl_3$) 7.0, 8H, m, phenyl; 5.8 and 5.2, 2H, d, d, vinyl; 4.1, 4H, s, $-CH_2CH_2-$; 1.8 3H, s, $CH_3$—IR: (Peak position ($cm^{-1}$), assignment) 1750, carbonyl; 1620, vinyl; 1220, C-O; 720, aromatic.

EXAMPLE 2

Polyethylene glycol-methacrylate phenothiazine
N-carboxylate bis ester (II)

a.) Bulk polymerization: A degassed mixture of monomer (I) and 0.5% azobisisobutyronitrile (AIBN) were heated in a sealed tube at 70° C. Polymerization started immediately and a colorless, clear, tough polymer was obtained in 1 hour. An increase in pressure was observed in the tube. Dissolution in chloroform and precipitation with pentane gave a colorless, powdery polymer which was best separated by centrifugation. The mother liquor showed the presence of phenothiazine, but no unreacted monomer could be detected (TLC silica gel, carbon tetrachloride). A higher polymerization temperature polymer was obtained as an expanded form and pressure build-up during polymerization was also highest.

b.) Solution polymerization: To a degassed, 15% solution of monomer (I) in tetrahydrofuran, 1% (based on monomer) AIBN was added and the mixture was heated in a sealed tube at 45° C. for 10 hrs. The solution became viscous in 20 min. The polymer was precipitated by addition of ethanol to give a white powder in 63% yield. No pressure build-up was observed.

NMR: ($CDCl_3$) 7.0, broad, m, phenyl; 4.1, broad, s, $-CH_2-CH_2-$; 1.0, broad, s, backbone methylene.
IR: 1750, carbonyl; 1200, C-O; 770, aromatic.

EXAMPLE 3

Glycidyl phenothiazine N-carboxylate (III)

Phenothiazine N-carbonyl chloride, 1.5 g (6 mmol) and 6 mmol of glycidol were heated in a reflux apparatus equipped with a drying tube at 90° C. for 10 hours on an oil bath. Then the reflux apparatus was converted for distillation and the excess glycidol was removed under vacuum at this temperature. The resulting brown oil solidified upon cooling and was dissolved in chloroform, treated with charcoal, dried and evaporated to dryness. Recrystallization of the resulting solid from ethanol gave the product: 1.0 g (55%), tan crystals m.p. 92°–94° C. NMR: ($CDCl_3$) 7.3, 8H, m, phenyl; 4.5, 2H, d, d, exocyclic $-CH_2-$; 3.4, 1H, m, CH; 2.9, 2H, m, endocyclic $-CH_2-$. IR: 1710, carbonyl; 1250, 900, oxirane; 750, aromatic.

EXAMPLE 4

Poly-glycidyl phenothiazine N-carboxylate (IV)

Glycidyl ester (III), 0.4 g was dissolved in freshly distilled and dried dichloromethane in a septum bottle and brought to 0° C. Boron trifluoride-etherate, 0.03 ml, was introduced with a syringe and an immediate cloudiness was observed. After 2 hours at 0° C. and 12 hours at room temperature, the solvent was removed to give a tan colored polymer. 0.35 g (88%).

NMR: (acetone) 7.2, broad, m, phenyl; 4.2, broad, m, pendant $-CH_2-$; 2.9–3.4, broad, m, backbone protons.
IR: 3300, end group-OH; 1730, carbonyl; 1085, C-O-C; 720, aromatic.

EXAMPLE 5

Phenothiazine N-carboxylate diethanolamide (V)

Phenothiazine N-carbonyl chloride, 2.6 g (0.01 mole) and diethanolamine, 2.9 g (0.02 mole) were dissolved in 18 ml benzene and refluxed for 10 hours. The chloride dissolved immediately as the color turned from green to brown. At the end of the reaction period the mixture was cooled to 0° C. and washed three times with ice water with vigorous stirring. The resulting gummy solid was taken up in dichloromethane, treated with charcoal to give the product: white crystals, 1.9 g (55%), m.p.63–67%.

NMR: ($CDCl_3$ 7.1, 8H, m, phenyl; 3.6, 8H, $A_2B_2$, $-CH_2-CH_2-$.
IR: 3300, $-OH$; 1730, carbonyl; 730, aromatic.

EXAMPLE 6

Polyurethane of phenothiazine N-carboxylate
diethanolamide (VI)

Amide (V), 0.2 g (0.6 mmol) and toluene-2,4-diisocyanate (TDI), 0.1 g (0.6 mmol) were mixed, degassed, sealed and heated at 110° C. for 2 hours. An amber colored, clear and tough polymer was produced which was dissolved in chloroform and precipitated with pentane to give the product: white powder, 0.18 g.

NMR: ($CDCl_3$) 7.0, broad, phenyl; 2.4, broad, $-CH_2-CH_2-$.
IR: 3300,N-H; 1750, 1770, carbonyl; 770, aryl.

EXAMPLE 7

Phenothiazine N-carboxylate-polyvinyl alcohol
polyester (VII)

Polyvinyl alcohol, 0.3 g (6.8 mmol hydroxyl) was dissolved in 7 ml dimethylsulfoxide (DMSO) by heating at 70° C. for 1 hour with stirring. Phenothiazine N-carbonyl chloride, 1.5 g (6 mmol) was added in portions. Color changed from green to red and gas evolution could be observed. After 4 hours at 110° C. the mixture was cooled and poured into excess water to yield a light blue and very fine precipitate. The mixture was centrifuged and the recovered solid was washed with water to give 1.1 g (60%) blue powder after vacuum drying. The polymer turned dark blue upon exposure to light.

NMR: (DMSO) 6.9, broad, m, phenyl; 3.0, broad, s, $-CH-$; 1.8, broad, s, $-CH_2-$. Integration corresponds to 85% substitution. IR: 3300, residual-OH; 1730, carbonyl; 750, aromatic.

The polymers of the invention, after doping to render them conductive, can be used in applications such as photoconductors, in electromagnetic interference shields, to dissipate static electricity whereby the polymer is used in a paint or coating over the object generating the static electricity, and in heavy metal waste treatment.

The waste treatment applications specifically include use of the undoped polymer as a column bed which provides a means for reduction of metal oxides in solution (e.g., $Cr^{+6}$ to $Cr^{+3}$), whereby the polymer acts as an electron donor.

Further applications of the conductive polymer of the invention include use in solar cells and in electrochromic display devices.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A compound having the formula:

$R_1XR_2$ wherein $R_1$ is a group with monomer functionability capable of homo- or copolymerization and is selected from the group consisting of alkyl groups and mono epoxy groups, x is a divalent moiety pendant from $R_1$ and selected from the group consisting of
   —$COOR_5O$—, $R_6O$— and —O—, $R_2$ is

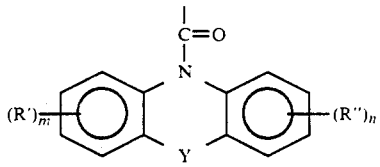

$R_5$ and $R_6$ are alkylene from 1 to 5 carbon atoms, m and n are separately integers from 0 to 4, R' and R" are separately alkyl from 1 to 5 carbon atoms, oxyalkyl from 1 to 5 carbon atoms or halogen, and Y is carbon or a heteroatom selected from N, O and S.

2. A compound as claimed in claim 1, wherein said compound comprises ethylene glycol-methacrylate phenothiazine N-carboxylate bis ester.

3. A compound as claimed in claim 1, wherein said compound is glycidyl phenothiazine N-carboxylate.

4. A compound having the formula:

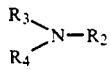

wherein $R_3$ and $R_4$ are separately hydroxyalkyl having from 1 to 5 carbon atoms,
   $R_2$ is

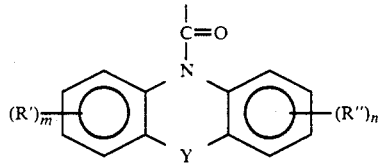

m and n are separately integers from 0 to 4, R' and R" are separately alkyl from 1 to 5 carbon atoms, oxyalkyl from 1 to 5 carbon atoms or halogen, and Y is carbon or a heteroatom selected from N and O.

* * * * *